United States Patent [19]

Thompson et al.

[11] Patent Number: 4,916,057

[45] Date of Patent: Apr. 10, 1990

[54] CHLAMYDIA ASSAY EMPLOYING BASE TREATMENT

[75] Inventors: Jeffrey A. Thompson, Richfield; Patrick A. Mach, Shorewood; Howard R. Soule, Minnetonka, all of Minn.

[73] Assignee: Kallestad Diagnostics, Inc., New York, N.Y.

[21] Appl. No.: 161,576

[22] Filed: Feb. 29, 1988

[51] Int. Cl.$^4$ ............... G01N 33/569; G01N 33/571
[52] U.S. Cl. ..................................... 435/7; 436/510; 436/825; 436/811
[58] Field of Search ............ 435/7; 436/510, 825, 436/826, 811, 174, 175

[56] References Cited

U.S. PATENT DOCUMENTS

| | | | |
|---|---|---|---|
| 4,056,608 | 11/1977 | Ullman et al. | 436/825 |
| 4,427,782 | 1/1984 | Caldwell | 435/7 |
| 4,497,899 | 2/1985 | Armstrong et al. | 436/825 |
| 4,617,264 | 10/1986 | Whiteley et al. | 435/7 |
| 4,652,518 | 3/1987 | Makela et al. | 436/510 |
| 4,663,291 | 5/1987 | Rose | 436/825 |
| 4,766,065 | 8/1988 | Mosier et al. | 435/7 |

OTHER PUBLICATIONS

The Manual of Clinical Microbiology, pp. 163–164 (3rd Ed. 1980).

*Primary Examiner*—Esther M. Kepplinger
*Attorney, Agent, or Firm*—James R. Haller; Mary P. Bauman; Gregory P. Kaihoi

[57] ABSTRACT

An immunoassay procedure for the detection of chlamydia trachomatis antigen in a urogenital clinical specimen including a method for substantially eliminating the occurrence of false negative and false positive results of the immunoassay procedure. The method comprises treating a patent specimen with an aqueous solution having a final concentration of 0.1M NaOH or 0.1M KOH and then neutralizing the specimen-containing solution before conducting the immunoassay.

4 Claims, No Drawings

CHLAMYDIA ASSAY EMPLOYING BASE TREATMENT

FIELD OF THE INVENTION

This invention relates to an immunoassay procedure for the detection of *Chlamydia trachomatis* antigen in a urogenital clinical specimen.

BACKGROUND OF THE INVENTION

*Chlamydia trachomatis* is the etiologic agent in several types of human infection including urethritis, mucopurulent cervicitis in females, and inclusion conjunctivitis and pneumonitis of newborns.

While anti-chlamydial drug therapy exists, many chlamydial infections go untreated because of the limitations connected with current diagnostic methods. This is a significant problem for females where the majority of cervical infections are asymptomatic and, if untreated, may progress to pelvic inflammatory disease which can result in infertility. A commonly used method for detecting chlamydia depends upon culture techniques. This technique is laborious and time-consuming. Thus, a reliable, rapid and inexpensive test to identify the organism is desirable so that proper therapy can be initiated.

Immunoassays such as enzyme and direct fluorescent immunoassays detecting various chlamydial antigens, such as lipopolysaccharide (LPS) and major outer membrane protein (MOMP), are currently used to detect the presence of chlamydia in patient samples. In the case of enzyme immunoassay, samples are commonly pretreated with detergents to solubilize MOMP or LPS antigens for subsequent antibody binding. However, false negative and false positive results from such immunoassays tend to occur in significant numbers. Pretreatment of specimens with detergent does not eliminate the occurence of such false positive and false negative results.

SUMMARY OF THE INVENTION

It has now been discovered that detergent extraction of *Chlamydia trachomatis* from patient specimens can take place under strongly basic conditions and that these conditions drastically reduce the incidence of false positive and false negative results in certain immunoassay formats.

The occurrence of false negative and false positive results in immunoassays for chlamydia antigen in a patient specimen can be reduced, in accordance with the invention, by extracting patient specimens in a strong base solution, then neutralizing the specimen solutions before conducting the assays. The strong base may be sodium hydroxide (NaOH) or potassium hydroxide (KOH). Ammonium hydroxide (NH$_4$OH) and bases of similar strengths are less effective. The strong base solution desirably comprises a concentration of strong base of at least about 0.05M and preferably of at least 0.1M or equivalent.

DETAILED DESCRIPTION OF THE PREFERRED EMBODIMENT

The methods of this invention can be used with patient specimens obtained from patients suspected of having a chlamydial infection utilizing conventional medical and microbiological techniques. Such specimens include swab specimens taken from the eye, nares at the back of the nose, cervix, urethra, throat or rectum. The method is particularly useful with urogenital swab specimens.

In one method of this invention, a solution of a strong base with an appropriate extraction detergent such as those commonly used in extraction of membrane components i.e., 3[(3-cholamidopropyl)-diamethylammonio]-1-propane sulfonate (CHAPS), is added to a tube containing a urogenital swab. The swab is allowed to stand in this solution and mixed well followed by expulsion of excess liquid in the swab and removal of the swab. The solution in the tube is then neutralized. An appropriate volume of the neutralized solution is then used in the performance of a standard sandwich type enzyme immunoassay (EIA) to detect the presence of a chlamydia antigen.

In a modification of the invention, a solution of the appropriate extraction detergent is added directly to a tube containing a patient swab. The patient swab is allowed to stand in this solution with mixing followed by expulsion of excess liquid from the swab and removal of the swab. A one tenth volume of strong base at a minimal concentration of 1.0M is then added to the patient extract to provide a final concentration of 0.1M base, equivalent to the concentration of base used in the first method. The sample is allowed to stand, mixed, and then neutralized. An appropriate volume of the neutralized solution is then used in a standard sandwich-type EIA to detect the presence of a chlamydia antigen.

The sandwich type EIA is preferably one in which an antibody:antigen:antibody sandwich is formed on a solid support. Typically, an antibody that will specifically bind chlamydia is bound on a solid support such as filter paper, test tubes made from polyethylene, polystyrene, polypropylene or other suitable materials, latex particles, glass beads, magnetic particles or the like. Sample suspected of containing chlamydia is contacted with the solid support and chlamydial antigens present in the sample will bind to the bound antibody during a suitable incubation period. The solid support is washed to remove residual sample and unbound antigen, if any, and then contacted with a solution containing a known amount of a second antibody also specific to chlamydia labeled directly or indirectly (as with an antibody to the second antibody) with an enzyme. If the second antibody is directly labeled then after the solid support is washed enzyme substrate is added to the solid support and an enzyme determination performed by conventional colorimetric, or spectrophotometric techniques. If the second antibody is unlabeled then a labeled antiglobulin directed against the second antibody is added, the solution is allowed to stand for a predetermined time and the solid support is washed. The amount of labeled antibody is the determined by conventional techniques.

Antibody specific to chlamydia may be raised in a human or nonhuman species such as rabbit, goat, horse, sheep, guinea pig, etc by immunization with elementary bodies of one or more strains of *Chlamydia trachomatis* in accordance with known techniques. Monoclonal antibody to chlamydia may also be used with the method of this invention.

Chlamydia antigens useful with this invention include any antign common to the prevalent strains of *Chlamydia trachomatis*. Such antigens are readily ascertained by one of ordinary skill in the art and include for example, LPS and MOMP. Enzymes useful with this invention may include for example horseradish peroxidase, alkaline phosphatase, Beta-galactosidase and the like.

Enzyme immunoassays are well known in the diagnostic field and need not be described in further detail.

Without being bound by the following explanation, we believe the patient sample treatment of the invention eliminates or inactivates substances in the sample that interfere with immunological assays to cause false positive and false negative results. These interfering substances seem to be eliminated when the pH of the solution is raised to a level at or above pH 12 and then neutralized.

False positive and false negative results obtained using an immunoassay may be detected by various methods, i.e., direct fluorescent analysis, culturing techniques and the like. Direct fluorescent labeling techniques have been used to determine whether chlamydia is present in a sample as follows. Antibody that binds specifically to chlamydia labeled with a fluorescent agent was obtained. Labeled antibody of this type is commercially available from Kallestad Diagnostics or Syva Company. A volume of specimen extract is obtained and centrifuged to form a pellet comprised of chlamydia elementary bodies and debris from the sample. The pellet is resuspended in a minimal volume of buffer, spotted on a microscope slide, fixed with methanol and stained with the labeled antibody reagent. The antibody binds to the chlamydia, if any, on the slide. The slide is then read using an appropriate microscope to determine whether chlamydia is present. In samples not treated with a strong base solution in accordance with the invention prior to performing the EIA, a significant number of samples that tested positive under the direct fluorescence method yielded negative EIA results. Similarly, several samples that were negative using the direct fluorescence method were positive by the EIA method.

Signal recovery studies demonstrated the existence of functional false negatives using patient specimens extracted into a buffered detergent solution as in the second method described above. Functional false negative samples produced low EIA absorbance value even where chlamydial antigen was exogenously added to the sample.

Four equal volume aliquots of each sample that had been extracted into an aqueous solution were removed. Two aliquots received a one tenth volume of purified chlamydia elementary bodies (spiked) and the other two aliquots received an equal volume of buffer (unspiked). One spiked and one unspiked aliquot were then treated with a one tenth volume of 1.0M NaOH and the other aliquots were treated with the same volume of deionized water and allowed to stand for 10 minutes. The aliquots treated with base were then neutralized by adding 0.10 ml of 1.0M HCl (diluted in 1.0M Tris HCl, previously at pH 8.0) to the sample and the solution vortexed for ten seconds. The untreated aliquots were diluted with an equal volume of 1.0M Tris HCl buffer. After neutralization, all the aliquots were tested in a chlamydia specific EIA. Without strong base pretreatment, exogenously added chlamydia was not detected in a significant number of patient samples, as is shown in Table 1. With strong base pretreatment, however, exogenously added chlamydia was detected in all samples.

TABLE 1

ELIMINATION OF FALSE NEGATIVE RESPONSES BY BASE TREATMENT

| Patient number | response | Absorbance Value | | | |
|---|---|---|---|---|---|
| | | Neutral pH | | Basic pH | |
| | | with EB's | w/o EB's | with EB's | w/o EB's |
| 1 | D | .680 | .080 | 1.186 | .115 |
| 2 | ND | .108 | .093 | 1.338 | .098 |
| 3 | ND | .123 | .131 | 1.415 | .245 |
| 4 | D | .861 | .080 | 1.429 | .184 |
| 5 | ND | .158 | .081 | 1.355 | .101 |
| 6 | D | 1.013 | .094 | 1.299 | .116 |
| 7 | D | 1.030 | .090 | 1.444 | .095 |
| 8 | D | 1.154 | .088 | 1.398 | .109 |
| 9 | D | 1.013 | .109 | 1.422 | .087 |
| 10 | ND | .069 | .111 | 1.346 | .103 |

EB—Elementary Body
D—EB's Detected
ND—EB's Not Detected

Functional false positive samples were also evaluated using patient specimens extracted into a buffered detergent solution as decribed in method 1 above. EIA absorbance values from clinical specimens have been compared with results obtained using direct fluorescent techniques for the same specimens to produce a absorbance level (cutoff) above which samples will be considered positive and below which samples will be considered negative.

Two equal volume aliquots of each sample extracted into solution were removed. One aliquot received a one tenth volume of 1.0M NaOH and the other aliquot received the same volume of deionized water. The aliquots were allowed to stand for 10 minutes. The aliquot treated with the base was neutralized as described above and the other aliquot was diluted with an equal volume of buffer. The samples were assayed in a conventional sandwich-type EIA using polyclonal anti-chlamydia antibody and horseradish peroxidase (HRP) labeled detection antibody diluted into conventional diluent buffer. The absorbance value cutoff for this experiment was 0.22. The results, shown in Table 2, show that with a significant number of samples, absorbance values from non-base-treated specimens were spuriously high and the base treatment of these samples avoided this result. Spurious values such as those demonstrated below may have led to the erroneous conclusion that chlamydia antigen was present in the sample.

TABLE 2

ELIMINATION OF FALSE POSITIVE RESPONSES BY BASE TREATMENT

| Patient Number | Absorbance Value | |
|---|---|---|
| | Neutral pH | Basic pH |
| 1 | .963 | .312 |
| 2 | .105 | .163 |
| 3 | .095 | .087 |
| 4 | .101 | .206 |
| 5 | .121 | .099 |
| 6 | 2.058 | .200 |
| 7 | .108 | .109 |
| 8 | 1.014 | .222 |
| 9 | .953 | .567 |
| 10 | .262 | .132 |

Experiments utilizing several different bases demonstrated that strong bases such as sodium hydroxide and potassium hydroxide which completely ionize in water (i.e. solutions of 1.0N produce a pH of 14.0) were the most effective. Weaker bases such as ammonium hydroxide, trisodium phosphate, sodium carbonate, and amine-containing compounds were not as effective. The weaker bases all have $pK_a$ values less than 13.

The invention is further demonstrated by the following illustrative examples.

EXAMPLE 1

A urogenital swab specimen was obtained from a patient and placed in a 12×75 mm glass test tube. A 1.0 ml volume of 0.1M NaOH or KOH with 0.005M disodium ethylenediaminetetracetic acid ($Na_2EDTA$) and 0.05% weight/volume CHAPS was added to the tube extract the sample from the swab.

The swab was allowed to stand in the above-described solution for at least ten minutes and vortexed and was wrung out against the side of the tube to expel absorbed liquid and discarded. 0.10 ml of 1.0M HCl or some other acid was added to the solution to neutralize the base. The neutralizing agent was added in a 2.0M tris(hydroxymethyl)-aminomethane hydrochloride (TrisHCL) solution initially at pH 8.0. The sample was vortexed for ten seconds to complete the neutralization process.

An appropriate volume of sample was removed from the tube for assay in a chlamydia specific EIA as described in Example 3.

EXAMPLE 2

A urogenital swab specimen was placed in a 12×75 mm test tube and extracted into a solution of 1.0 ml of 0.10M Tris HCl, 0.005M $Na_2EDTA$, 0.05% w/v CHAPS, pH 8.0. The swab was allowed to stand in that solution for at least 10 minutes and vortexed for about 30 seconds. After the swab was wrung out against the side of the tube to expel absorbed liquid, 0.100 ml of 1.0 M NaOH or 1.0 KOH was added to the sample and the tube was vortexed for another ten seconds. After ten minutes, 0.100 ml of 1.0M HCl diluted into 1.0M Tris HCl, pH 8.0 was added. The specimen containing sample was vortexed for ten seconds to complete the neutralization. An appropriate volume of sample was removed from the tube for use in a chlamydia specific EIA as described in Example 3.

EXAMPLE 3: IMMUNOASSAY.

Two hundred microliters of the pretreated specimen, a positive and a negative control were each added to an antibody-coated assay tube. After the sample was placed in the coated tube, the tube was shaken gently and allowed to stand at room temperature for about one hour.

100 microliters of polyclonal antibody specific for chlamydia, produced and purified using well known procedures equivalent to those described in H. D. Caldwell, C. Kuo and G. E. Kenny, 115 *Journal of Immunology*, pps. 969-975 (1975), was added to each tube, and each tube was gently mixed and allowed to stand for about an hour at room temperature. 100 microliters of horseradish peroxidase (HRP) conjugated to antibody directed against the chlamydia specific polyclonal antibody and obtained from commercial sources, such as Jackson Immuno Research Laboratories, Inc., was added to each tube. Each tube was gently mixed and allowed to stand for one hour at room temperature. The mixture in each tube was then removed and the tube washed thoroughly with deionized water. 500 microliters of freshly prepared substrate solution consisting of one part chromagen (3.0 mg/ml tetramethyl benzidine in 0.1M HCl) to 25 parts substrate buffer (0.05M sodium citrate, 0.05 M boric acid, 0.012% volume/volume hydrogen peroxide, pH 4.2) was added to each tube.

The enzyme reaction was allowed to proceed for 15 minutes and stopped with 1.0 ml of 1.0M sulfuric acid ($H_2SO_4$). The absorbence of the samples was spectrophotometerically at 450 nanometers. The color intensity is a function of the amount of chlamydia antigen present in the sample and the amount of antigen was determined accordingly.

While a preferred embodiment of the present invention has been described, it should be understood that various changes, adaptations and modifications may be made therein without departing from the spirit of the invention and the scope of the appended claims.

What is claimed is:

1. A method for substantially eliminating the occurrence of false negative and false positive results in an enzyme imunoassay for a chlamydia antigen in a patient specimen taken from the eye, nares at the back of the nose, cervix, urethra, throat or rectum comprising treating said specimen with an aqueous solution having a final concentration of not less than 0.1M NaOH or 0.1M KOH and then neutralizing the specimen-containing solution before conducting the immunoassay.

2. The method of claim 1 wherein the chlamydia antigen is a lipopolysaccharide.

3. The method of claim 1 wherein the specimen is an urogenital specimen.

4. The method of claim 3 wherein the specimen is a swab specimen.

* * * * *